United States Patent [19]

Greengarg

[11] Patent Number: 5,656,020

[45] Date of Patent: *Aug. 12, 1997

[54] LIFTING BELT, PANEL AND METHOD

[76] Inventor: Gerson M. Greengarg, 17063 Ryton La., Boca Raton, Fla. 33496

[*] Notice: The term of this patent shall not extend beyond the expiration date of Pat. No. 5,318,507.

[21] Appl. No.: 511,510

[22] Filed: Aug. 4, 1995

Related U.S. Application Data

[62] Division of Ser. No. 384,190, Feb. 6, 1995, abandoned, which is a continuation of Ser. No. 194,689, Feb. 10, 1994, abandoned, which is a division of Ser. No. 907,832, Jul. 2, 1992, Pat. No. 5,318,507.

[51] Int. Cl.$^6$ .................................... A61F 5/00
[52] U.S. Cl. ................................... 602/19; 2/48
[58] Field of Search ................... 602/19; 128/96.1, 128/99.1, 100.1, 101.1, 874, 875; 2/48, 51, 102

[56] References Cited

U.S. PATENT DOCUMENTS

| | | | |
|---|---|---|---|
| 5,040,524 | 8/1991 | Votel et al. | 602/19 |
| 5,086,759 | 2/1992 | Buddingh | 602/19 |
| 5,111,806 | 5/1992 | Travis | 602/19 |
| 5,122,111 | 6/1992 | Sebastian et al. | 602/19 |
| 5,148,549 | 9/1992 | Syder | 602/19 X |
| 5,179,942 | 1/1993 | Drulias et al. | 602/19 X |
| 5,188,585 | 2/1993 | Peters | 602/19 |
| 5,188,586 | 2/1993 | Castel et al. | 602/19 |
| 5,205,815 | 4/1993 | Saunders | 602/19 |
| 5,241,704 | 9/1993 | Sydor | 602/19 X |
| 5,256,135 | 10/1993 | Avihod | 602/19 |
| 5,257,419 | 11/1993 | Alexander | 602/19 X |
| 5,302,171 | 4/1994 | Pearson et al. | 602/19 |
| 5,318,507 | 6/1994 | Greengarg | 602/19 |
| 5,399,150 | 3/1995 | Saunders | 602/19 |

*Primary Examiner*—Linda C. Dvorak
*Attorney, Agent, or Firm*—Jack E. Dominik

[57] ABSTRACT

Various combinations of a detachable back belt, a panel member, a lifting belt and suspenders are disclosed. The lifting belt has an elastic body portion with two ends to prevent the lifting belt from riding up the torso of the user. The panel member may be in the shape of an apron with the traditional lower pocket sections. The panel member may also have means for securing the suspenders thereto. Finally, a detachable back belt secures to the rear portion of the underlying lifting belt. The method of the invention is directed to applying the combination of apron, lifting belt, suspenders, and detachable back belt to the user by first placing the lifting belt about the user. Thereafter, the panel member is secured to the overlapped outer ends of the lifting belt, and the suspenders secured over the shoulders and to the panel member. Subsequently, the detachable back belt is secured to the lifting belt and to the panel member.

10 Claims, 5 Drawing Sheets

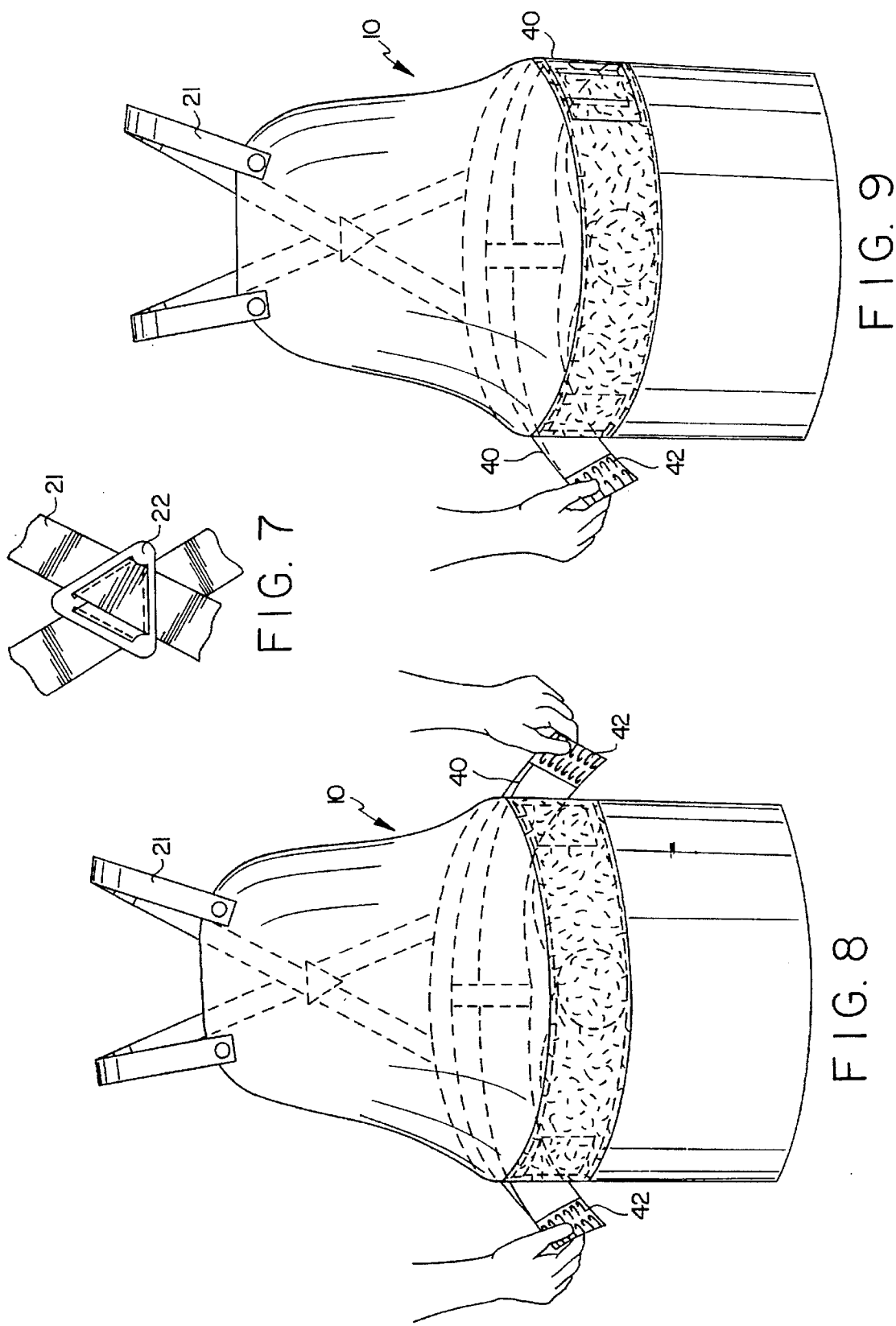

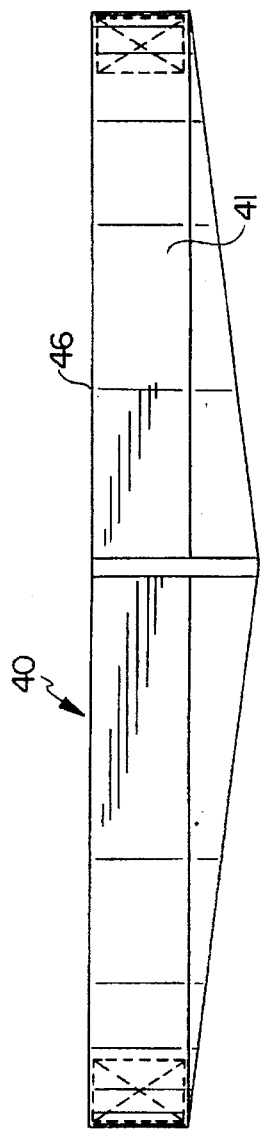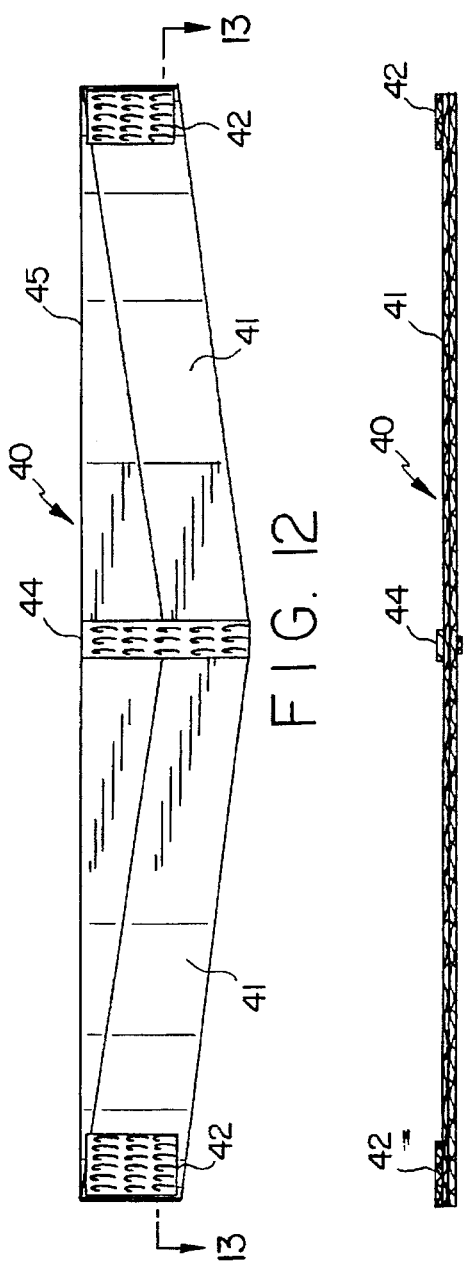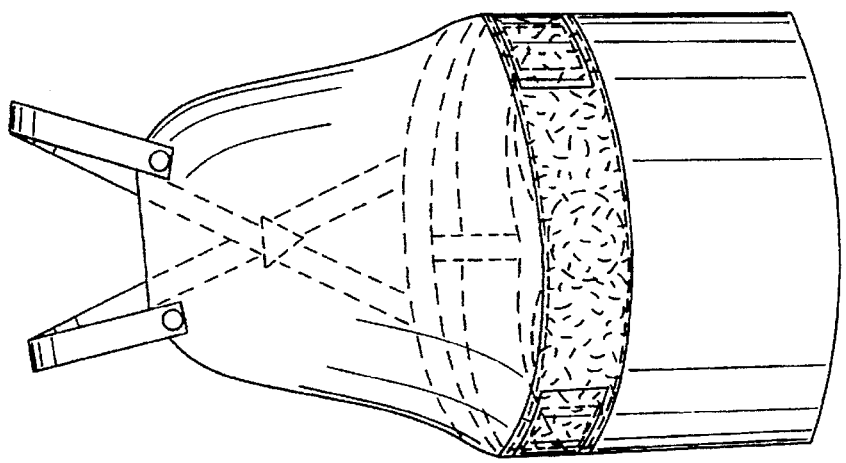

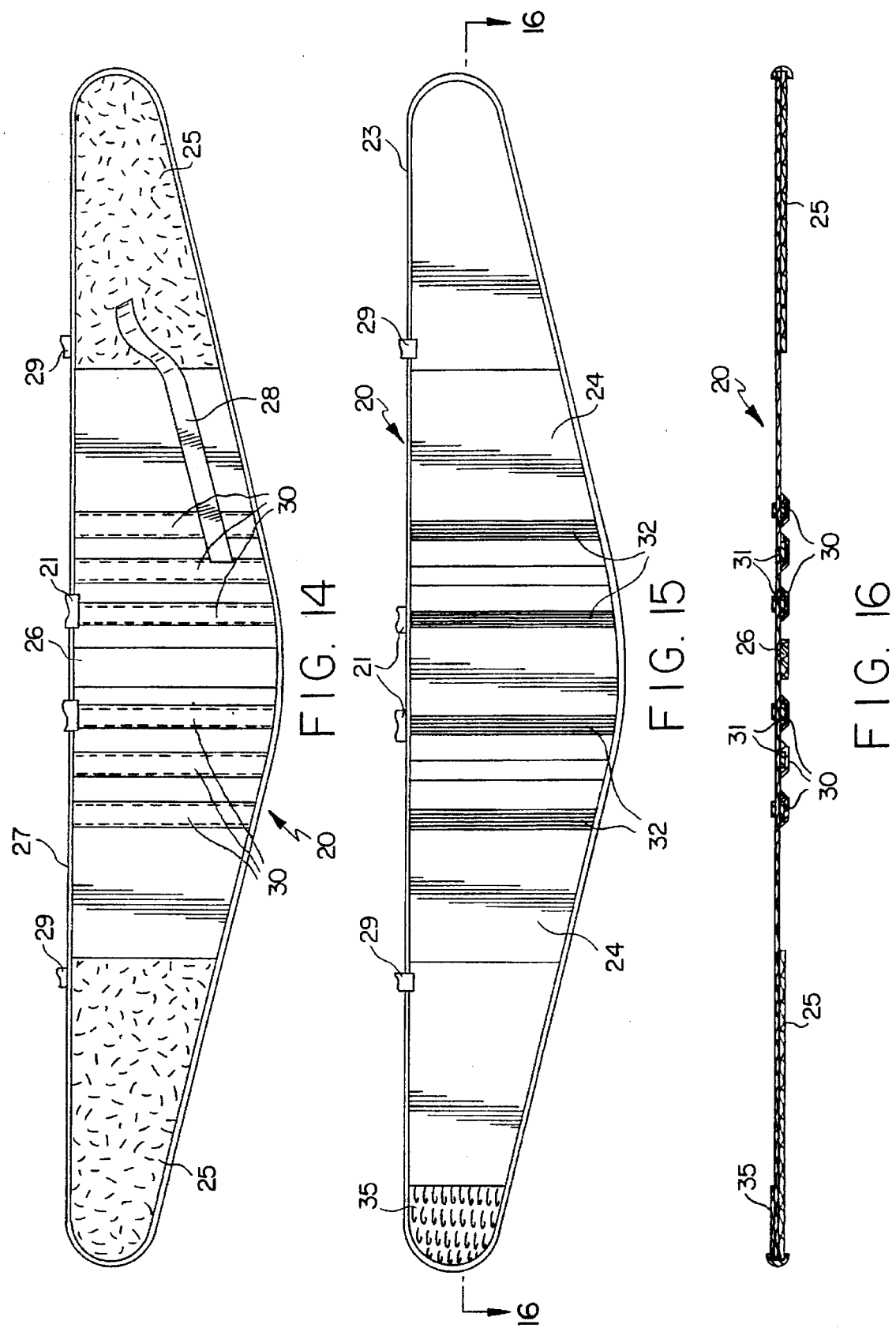

LIFTING BELT, PANEL AND METHOD

CROSS-REFERENCE TO RELATED APPLICATIONS

The present application is a divisional of application Ser. No. 08/384,190 filed Feb. 6, 1995, and entitled "Detachable Back, Belt, Apron, Method" by the same inventor herein, now abandoned, which in turn is a continuation of application Ser. No. 08/194,689 filed Feb. 10, 1994 "Detachable Back, Belt, Apron, Method" by the same inventor herein, now abandoned, which in turn is a divisional of application Ser. No. 07/907,832 filed Jul. 2, 1992, entitled "Detachable Back, Belt, Apron, Method" by the same inventor herein and now issued U.S. Pat. No. 5,318,507, issued Jun. 7, 1994.

FIELD OF THE INVENTION

The present invention relates to lifting belt assemblies of the type typically worn by warehouse workers, nurses, factory workers and the like where lifting is a common part of the duties and awkward positions should be anticipated.

SUMMARY OF THE PRIOR ART

The prior art abounds with elastic belts or leather bands secured around the lower lumbar region of the back with flat supports on the back portion and a detachable front portion for securing the same. Panel members, for example aprons, are often worn by the person using the belt. The panel member may be worn outside the belt, or sometimes inside the belt.

In many environments the aprons become soiled to the point where they cannot be cleansed, they are literally discarded. In such an environment, it is to be anticipated that the back of the belt of the user may very well become soiled. Accordingly, it is highly desirable to create an assembly of a panel member, lifting belt and detachable back belt to the end that the apron can be discarded, optionally the belt can be discarded, but the underlying lifting belt may be the subject of ongoing use by the worker.

SUMMARY OF THE INVENTION

The present invention is directed to various combinations of a detachable back belt, a panel member, and a lifting belt which is a direct body engaging member with ends that are closed underneath the panel member. The lifting belt has vertical stays, and an elastic body portion with belt loops to prevent the same from riding up the torso of the user. The panel member can be in the shape of an apron with the traditional lower pocket sections, and the panel member may also have means for securing to the suspenders which are an extension of the lifting belt. The front of the panel member is provided with a loop-hook engaging section in the shape of a transverse strap. Finally, a detachable back belt secures to the rear portion of the underlying lifting belt and wraps around the same to finalize the securement by overlapping the already assembled overlapping end portions of the lifting belt and securing the ends to the panel members transverse strap. A lifting belt hook central engaging member on the detachable belt engages the back of the lifting belt. The method of the invention is directed to applying the combination of a panel member, lifting belt, suspenders, and detachable back belt to the user by first putting on the apron. Thereafter, the lifting belt is slipped under the panel member, the suspenders secured over the shoulders, and the suspenders optionally adjusted at that time for the short chested or long torso person. Subsequently, the underlying lifting belt ends are overlappingly engaged to each other. Thereafter, the detachable back is secured to the lifting belt and panel member. Finally, just before using, the wearer will tighten the ends of the lifting belt, and then pull the ends of the detachable back belt snugly towards each other and overlie them on the loop portion of the front of the apron. The underneath portion of the apron and its lateral edges hook members engage the underlying lifting belt loop ends prior to the detachable back ends being secured over the front of the apron.

It is a principal object of the present invention to provide for a disposable panel member or to be used in combination with a lifting belt. A related and important object of the invention is to add to the combination of disposal panel member or apron and lifting belt a detachable back belt portion which assists in securing the lifting belt from a standpoint of utility, and yet can be thrown away if it becomes soiled to the degree of the apron while retaining the lifting belt. Since the cost of the replaceable apron and replaceable detachable back belt is perhaps one-third of the total cost of the original package, this occasions a savings in annual usage in those places where the aprons and/or detachable back belts must be discarded as often as once every three months.

Still another object of the present invention is to provide for continuity and overlapping relationship between all of the members including panel lifting belt, detachable back belt, and suspenders to the end that a coordinated securement is achieved by the user as dictated by the relationship of the elements of the three principle elements along with the suspenders.

An additional objective of the present invention is to provide a stand alone panel member such as an apron with an elastic neck band for applications where a lifting belt will not be worn, but the panel member can serve as a part of inventory adaptable for use with the lifting belt or without.

Yet another object of the present invention is to provide a lifting belt with a detachable belt which can be used without the use of an apron.

BRIEF DESCRIPTION OF THE DRAWINGS

The present invention will be better understood as taken in conjunction with the accompanying illustrative drawings, in which:

FIG. 7 is a partially broken view of the adjustment triangle used where the suspenders overlap each other in the back portion for accommodating various sizes of users;

FIG. 8 is a partially diagrammatic view illustrating the application of the detachable back belt to the front loop band of the panel member or apron;

FIG. 9 is a further sequential view from that shown in FIG. 8 illustrating the second hook inner end of the detachable belt being applied to the loop band in the front of the panel member or apron;

FIG. 10 is a final view illustrating the two ends of the detachable back secured to the front loop portion of the panel member or apron ready for lifting or for readjustment prior to lifting;

FIG. 11 is an outside view of the detachable back belt;

FIG. 12 is a wearer side plan view of the detachable back belt;

FIG. 13 is a transverse sectional view of the detachable back belt taken along section lines 13—13 of FIG. 12;

FIG. 14 is an outer face view of the lifting belt;

FIG. 15 is the wearer side or front elevation of the lifting belt showing the hook end at the left-hand portion of FIG. 15; and FIG. 16 is a transverse sectional view of the lifting belt taken along section lines 16—16 of FIG. 15.

DESCRIPTION OF PREFERRED EMBODIMENTS

Disposable Panel Member

Figure 1:
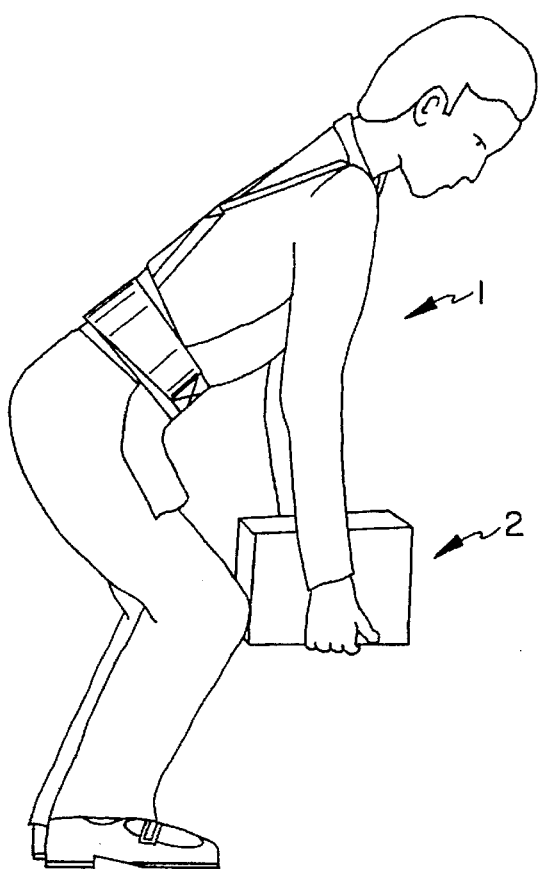
FIG. 1 shows a side elevation of a warehouse man lifting a load wearing an assembly illustrative of all aspects of the present invention.
Figure 2:
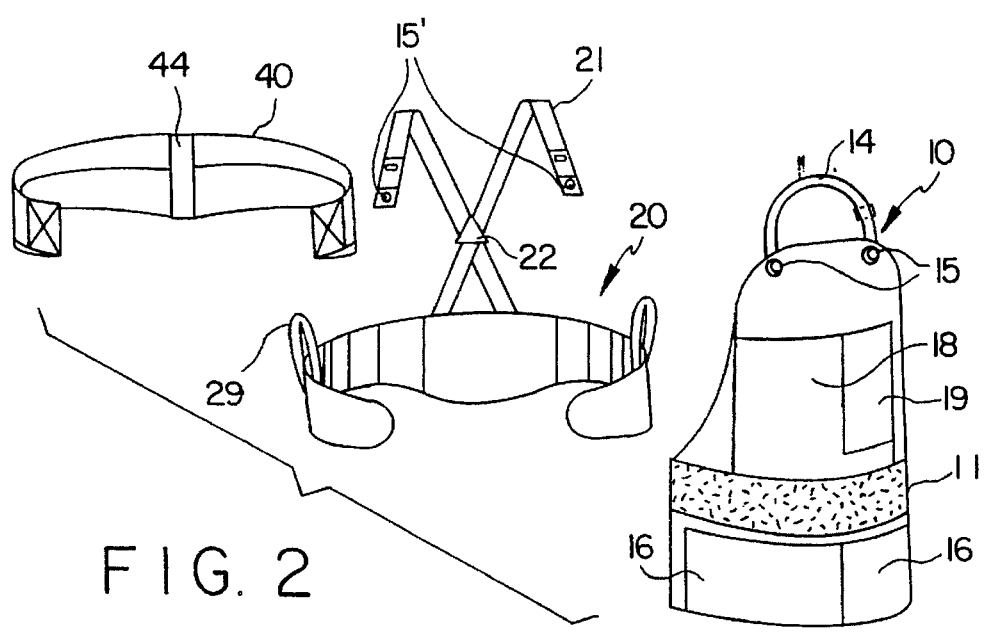
FIG. 2 is a partially diagrammatic view showing the panel member (or apron) lifting belt, and detachable back belt elements illustrative of the present invention.
Figure 6:
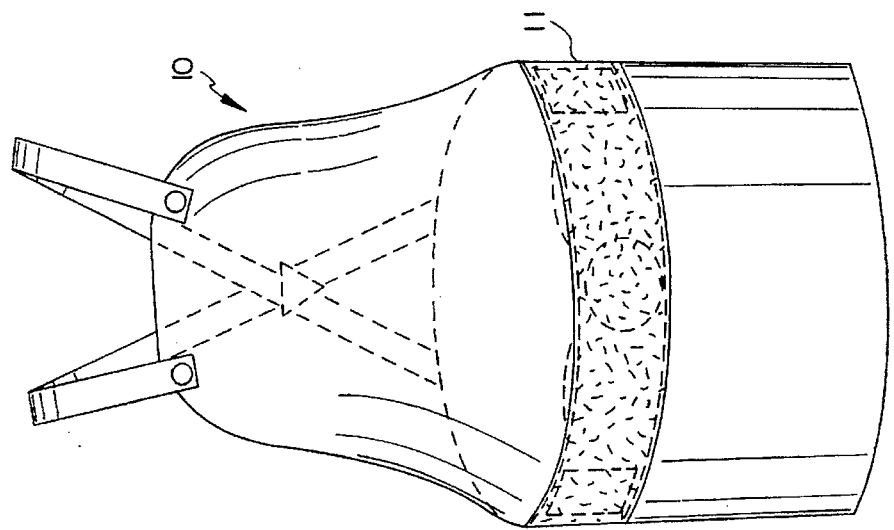
FIG. 6 is a further sequential view from that of FIG. 5 showing the apron after the lifting belt has been secured therebeneath.

The disposable panel member 10, e.g., an apron 10 illustrative of the present invention is shown on the warehouse man 1 of FIG. 1, and in diagrammatic partially perspective view at the right-hand portion of FIG. 2.

The underlying lifting belt 20 is shown in the middle portion of FIG. 2. It is provided with suspenders 21 and an adjustable triangle 22 where the suspender bands cross over. It has snap fasteners 15' for securing to the male fasteners 15 of the apron 10.

Finally, the entire assembly is completed by use of the detachable back 40, the central portion of which has a hook portion which engages the loop portion back of the lifting belt 20, and underlying hook elements at each end which overlappingly engage the loop band 11 of the apron 10. Where hook and loop are referred to they are removably secured opposite members. The reverse order of loop and hook is also contemplated and in addition any releasably secured structure in which both elements are the same.

The Panel Member

Figure 3:
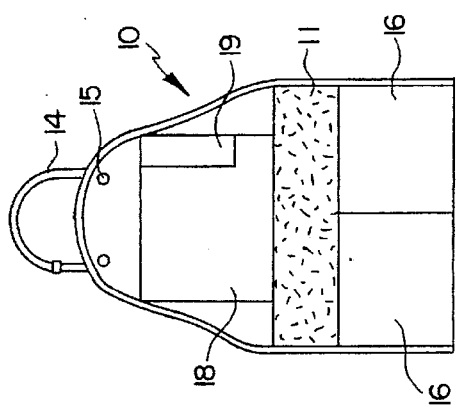
FIG. 3 is a plan view of the panel member or apron.
Figure 4:
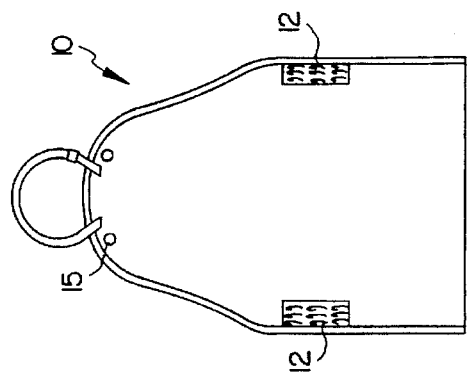
FIG. 4 is a plan view of the rear or wearer side of the apron of FIG. 3.
Figure 5:
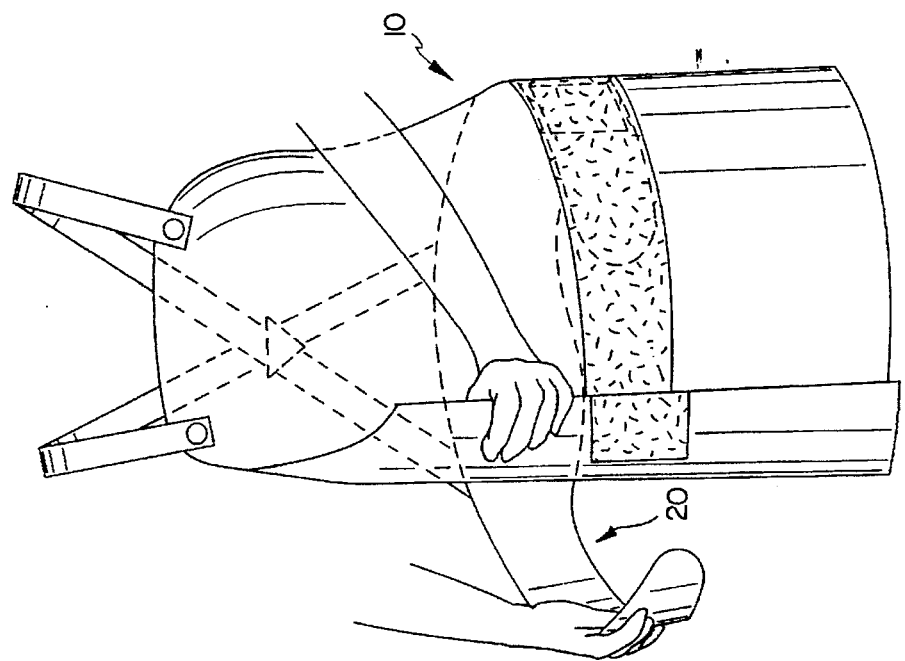
FIG. 5 is a partially diagrammatic view illustrating the application of the lifting belt after the apron has been placed over the wearer.

The stand along disposal panel member or apron 10 is best shown in FIGS. 3 and 4. There it will be seen that there is a preferred cotton body portion which has a transverse loop band 11 crossing the entire front portion. While the loop band 11 could be a hook band 11, the outer loops are less likely to abrade the arms of the wearer and less likely to entrap small particles of scrap. Beneath the loop band 11 are a pair of bottom pockets 16. An elastic loop 14 is provided at the upper portion of the panel member or apron with an adjustable feature for length of the user, neck size, and the like. Detachable male snaps 15 are provided to engage the ends of the suspenders. The traditional upper pouch 18 and pencil pocket 19 are provided in the front portion of the apron. The underneath portion or wearer side of the panel member or apron 10 is best illustrated in FIG. 4 where the elements are the same as those shown in FIG. 3 with the exception of the hook strips 12 which are provided to engage the loop end portions of the lifting belt 20 as will be described hereinafter. In addition, the suspenders 21 are provided with an adjustable triangle 22 as shown in FIG. 7 which permits raising and lowering the intersection of the two members of the suspender pair 21.

The Lifting Belt

Turning now to FIGS. 14–16, it will be seen that the lifting belt 20 has a pair of permanently secured suspenders 21 secured to its upper edge. The outer engaging face 23 is the one shown in FIG. 15. The body of the lifting belt 20 is formed of a Spandex-like foundation 24. Overlapping the two ends of the outer face 27 are loop end sections 25. To be noted is the non-elastic anchor band 28 which is secured at one end to one of the pockets 30 and at the other end to an adjacent loop end portion 25. The purpose of the non-elastic anchor band 28 is to prevent expanding or stretching the belt beyond its practical limits. Finally, belt loops 29 are provided at the beginning portion of the end loop sections 25 which have appropriate hooks in order to go over the belt of the wearer and then secure back again on the outer loop section 25.

Further to be noted particularly as in FIG. 16 provision is made for four of the pockets 30 to contain flexible stays 31. Optional rubberized stitching 32 is provided on the back engaging face to cooperate with the belt loops 29 to further secure the lifting belt 40 to the user and not ride up the torso.

The Detachable Back Belt

The detachable back belt 40 is best shown in FIGS. 11–13. There it will be seen that it is comprised of overlapping elastic band members 41 and terminates on the body side with a pair of panel members engaging means 42. The panel member engaging means 42 may be made of releasably securable material of the loop and hook type. The body side 45 also has a central lifting belt back loop-hook engaging element 44. The outer portion of the detachable belt 46 has no loop or hook elements, as shown in FIG. 11. Thus, it is less vulnerable to soil than the panel member which must have the releasably securable material in front.

The Method

The method of the present invention is illustrated by the sequences of applying the same in FIGS. 5 and 6, and 8–10. The panel member or apron 10 which is a stand alone apron can be used without the lifting belt 20 or the detachable belt 40. On the other hand, when the assembly is to be worn in its entirety, the panel member or apron 10 is first desirably put on by the user which includes inserting his head underneath the elastic neck band 14. Once the panel member or apron 10 is on, the lifting belt 20 is secured beneath the apron 10 with its one overlapping hook portion from the wearer side overlapping the opposite of the two end loop portions. The belt loops 29 are then applied to the belt of the user, and the suspenders 21 secured by means of snaps 15' to the male snaps 15 of the panel member or 10. The early lifting belt is secured underneath the panel member 10 and the apron loop band 11 is exposed throughout the entire frontal portion of the panel member 10. Some may find it easier to don the lifting belt 20 before the panel member 10. Thereafter the user is ready to apply the detachable back belt 40 as illustrated in FIG. 8. The detactable back belt 40 has two inner hook ends 42 which are secured to the outer loop band 11 of the panel member 10, first the one side as shown in FIG. 9, with the other side loop portion 42 in the hand of the user as shown in FIG. 9, and finally both ends are secured as illustrated in FIG. 10.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:

1. A lifting belt assembly, comprising, in combination, a lifting belt having an elastic body portion and ends, said ends having releasably securable means for overlappingly securing the ends to each other, and said ends also having outside securement portions for receiving further detachable secured members, a panel member having upper and lower ends with a mid-band of releasably securable material for receiving further detachable secured members, and a back belt having panel member engaging means for overlapping securement of the back belt to the releasably securable material of the panel member, whereby the panel member is secured between the underlying, overlapping lifting belt ends and the overlapping back belt ends and is thereby adapted to be spaced while in use from the waist of a user by being sandwiched between the lifting belt ends and the back belt ends.

2. The lifting belt assembly of claim 1 wherein the panel member is in the shape of an apron.

3. The lifting belt assembly of claim 1, further comprising, a suspender assembly having means for attaching the suspenders to the lifting belt and to the panel member, whereby the user can secure the panel member to his or her chest by attaching the suspenders to the lifting belt and to the panel member.

4. A lifting belt assembly for securement to a wearer for purposes of assisting the wearer in the lifting of loads, said assembly comprising, in combination, a lifting belt having an elastic body portion and ends, said ends having overlappingly releasably securable means for securing the ends to each other and having outside securement portions for receiving further detachable secured members, a panel member having an inner surface and an outer surface with that surface which is worn next to the wearer being the inner surface, said panel member having upper and lower ends with a mid-band of releasably securable material on its outer surface for receiving further detachable secured members, and said panel member also having releasably securable material on its inner surface opposite the mid-band for releasably securing the panel to the outside securement portions of the overlapped ends of the lifting belt, and a back belt having panel member engaging means for overlapping securement of the back belt to the mid-band of releasably securable material of the underlying panel member, whereby the lifting belt is secured to the waist of the wearer by overlappingly securing the ends to each other, the panel is secured to the overlapped ends of the lifting belt, and the back belt is then secured about the waist of the wearer and to the releasably securable material of the underlying panel member, thereby sandwiching the panel member between the underlying, overlapping lifting belt ends and the overlapping back belt ends.

5. The lifting belt assembly of claim 4 wherein the panel member is in the shape of an apron.

6. The lifting belt assembly of claim 4, further comprising, a suspender assembly having means for attaching the suspenders to the lifting belt and to the panel member, whereby the wearer can secure the panel member to his or her chest by attaching the suspenders to the lifting belt and to the panel member.

7. A method of securing a lifting belt to both a panel member and a back belt, said lifting belt and said back belt having panel member-engaging ends of releasably securable material, and said panel member having a front side and a rear side, with that side which faces away from a user to which it is connected being the front side, said panel member also having a mid-band of releasably securable material across the front side and releasably securable material on the rear side, said method comprising the steps of:

positioning the lifting belt in place on the user by overlapping the ends of the lifting belt each against the other, positioning the panel member over the lifting belt and securing the releasably securable the panel member to the releasably securable material of the lifting belt, and securing the panel member by wrapping the back belt around the user and engaging the panel member engaging ends of releasably securable material with the releasably securable material across the front side of the panel member, thereby sandwiching the panel member between the underlying lifting belt and the outer back belt.

8. A method of securing a combination of three elements, which are a lifting belt, a panel member and a back belt, to a user for purposes of assisting in lifting loads, said lifting belt having two outer ends with a front and rear side, with that side which faces away from the user being the front side, and with each of the two outer ends having releasably securable material on its front side and one of which outer ends also having releasably securable material on its rear side, said panel member having a front and rear side with that side which faces away from the user being the front side of the panel member, each of which sides of the panel member has releasably securable material, and said back belt having releasably securable members for engaging the panel member, said method comprising the steps of:

positioning the lifting belt in place on the user and then removably securing the same to the user by overlapping the outer ends of the lifting belt against each other by engaging the releasably securable material on the rear side of one of the outer ends of the lifting belt with the releasably securable material on the front side of the other outer end of the lifting belt, positioning the panel member over the user and removably securing the same by engaging the releasably securable material on the rear side of the panel member to the releasably securable material on the overlapped, front sides of the outer ends of the lifting belt, and securing the entire combination by wrapping the back belt around the user and engaging its two releasably securable members with the releasably securable material on the front side of the panel member.

9. A method of securing a combination of four elements which are a lifting belt, a panel member, a suspender assembly and a back belt to a user for purposes of assisting in lifting loads, said lifting belt having two outer ends with a front and rear side, with that side which faces away from the user being the front side, and with each of the two outer ends having releasably securable material on its front side, and one of which outer ends also having releasably securable material on its rear side, said panel member having a front and rear side with that side which faces away from the user being the front side of the panel member, each of which sides of the panel member has releasably securable material, and said back belt having releasably securable members for engaging the panel member, said method comprising the steps of:

positioning the lifting belt in place on the user and then removably securing the same to the user by overlapping the outer ends of the lifting belt against each other by engaging the releasably securable material on the rear side of one of the outer ends of the lifting belt with the releasably securable material on the front side of the other outer end of the lifting belt, positioning the panel member over the user and removably securing the same by engaging the releasably securable material on the rear side of the panel member to the releasably securable material on the overlapped, front sides of the outer ends of the lifting belt, securing the suspenders to the lifting belt and to the user, and securing the entire combination by wrapping the back belt around the user and engaging its two releasably securable members with the releasably securable material on the front side of the panel member.

10. A method for securing a combination of independent elements, which are a panel member, a lifting belt, a suspender assembly, and a detachable back belt, to a person for purposes of assisting in lifting loads, in which the lifting belt has two outer ends with a front and rear side, with that side which faces away from the user being the front side, and with each of the two outer ends having releasably securable material on its front side, and one of which outer ends also having releasably securable material on its rear side, said panel member having a front and rear side with that side which faces away from the user being the front side of the panel member, each of which sides of the panel member having releasably securable material, said suspender assembly being secured to the lifting belt, and said detachable back belt having releasably securable member for engaging the panel member, said method comprising the steps of:

positioning the lifting belt in place on the user and then overlapping the outer ends of the lifting belt against each other, positioning the panel member over the user and securing the releasably securable material on the rear side of the panel member to the overlapped, front sides of the outer ends of the lifting belt, securing the suspenders attached to the lifting belt to the user, and securing the entire combination by wrapping the detachable back belt around the user and engaging its two releasably securable members with the releasably securable material on the front side of the panel member.

\* \* \* \* \*